United States Patent [19]

Dunn

[11] Patent Number: 5,009,888

[45] Date of Patent: Apr. 23, 1991

[54] THERAPEUTIC ENZYME-ANTIBODY COMPLEXES

[75] Inventor: Joseph T. Dunn, Holliston, Mass.

[73] Assignee: Genzyme Corporation, Cambridge, Mass.

[21] Appl. No.: 37,862

[22] Filed: Apr. 13, 1987

[51] Int. Cl.$^5$ .................. A61K 37/54; A61K 39/395; C12N 9/96

[52] U.S. Cl. .................. 424/94.3; 424/85.8; 424/94.63; 424/94.64; 435/188; 435/212

[58] Field of Search .............. 435/188, 212, 226, 215, 435/216; 424/85, 94.3, 94.63, 94.64

[56] References Cited

U.S. PATENT DOCUMENTS 4,179,337 12/1979 Davis et al. .................. 435/181
4,285,932 8/1981 Smith .................. 424/94

FOREIGN PATENT DOCUMENTS 0152736 8/1985 European Pat. Off. .

OTHER PUBLICATIONS

Zyk, "Modification of L-Asparaginase EC-2 by Homologous Antibodies", BBA 302: 420–428 (1973).
Sevilla et al., Biochem. Biophys. Res. Comm., "Plasminogen Activator-Anti-Human Fibrinogen Conjugate", 130: 91–96 (1985).
Maksimenko et al., Thromb. Res., "Water-soluble Urokinase Derivatives of Combined Action", 38: 277–288 (1985).
Maksimenko et al., Thromb. Res., "Water-soluble Urokinase Derivatives with Increased Affinity to the Fibrin Clot", 38: 289–295 (1985).
Rosenblum et al., Cancer Res., "Modification of Human Leukocyte Interferon Pharmacology with a Monoclonal Antibody", 45: 2421–2424 (1985).

Primary Examiner—Richard A. Schwartz
Assistant Examiner—S. L. Nolan
Attorney, Agent, or Firm—Fish & Richardson

[57] ABSTRACT

A complex of a therapeutically effective enzyme and a monoclonal antibody specific for the enzyme, the antibody being bound to the enzyme by immunoaffinity, the $K_D$ of the antibody/enzyme complex being at least $10^{-11}$M, or by covalent bonding the antibody being bound to the enzyme at a site on the enzyme which does not substantially interfere with the activity of the enzyme and which increases the in vivo half-life of the enzyme.

2 Claims, 1 Drawing Sheet

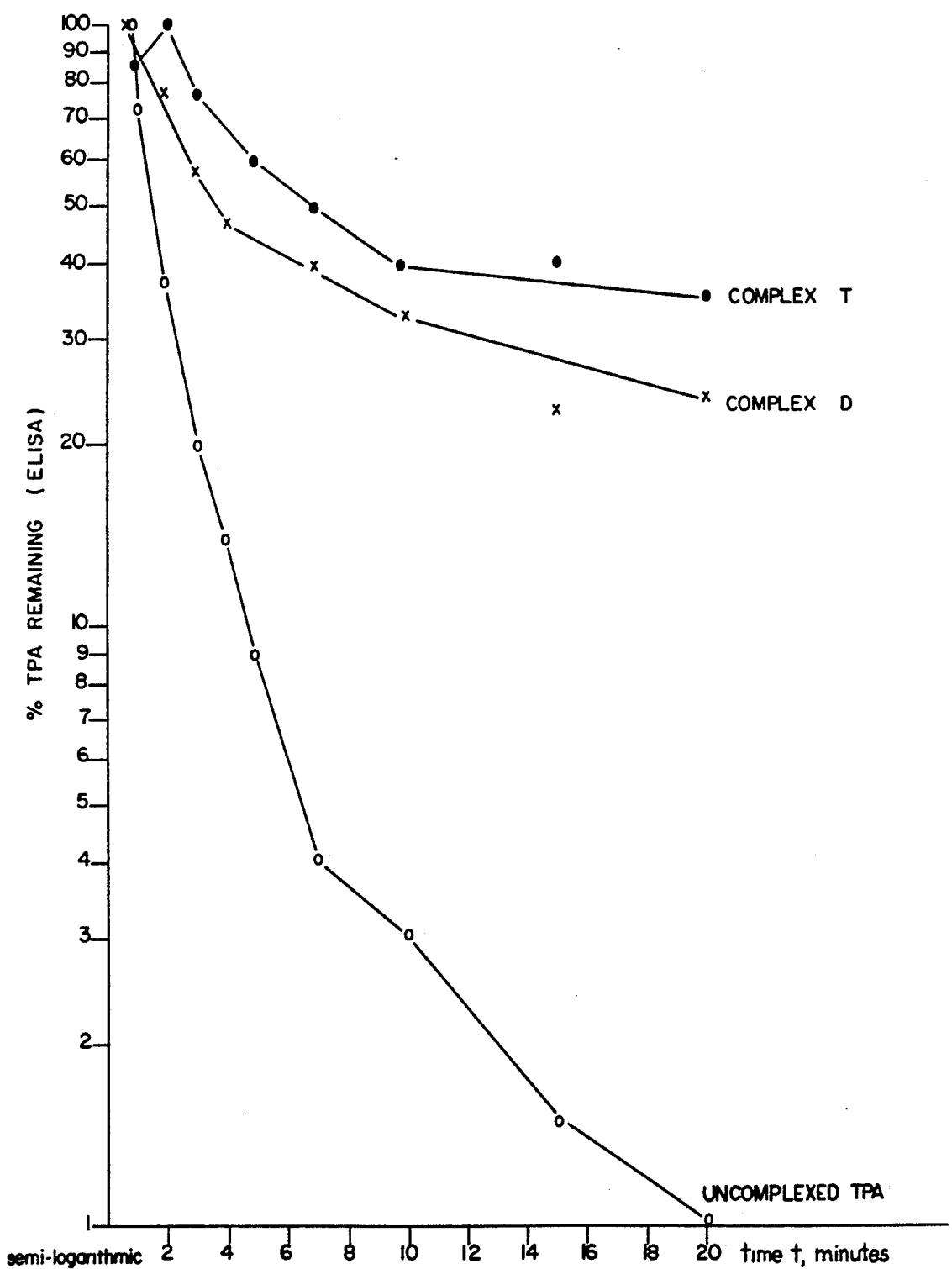
FIGURE

THERAPEUTIC ENZYME-ANTIBODY COMPLEXES

BACKGROUND OF INVENTION

The invention relates to increasing the half-life of circulating therapeutically effective enzymes in blood. As used herein, the term "therapeutically effective enzyme" means an enzyme which, when administered to a human patient, catalyzes a reaction beneficial to the health of the patient.

Therapeutic proteins have been modified in a number of instances to increase the circulatory half-life of the proteins. Davis et al. U.S. Pat. No. 4,179,337 describes covalently coupling proteins with polyethylene glycol to increase the circulation half-life of the protein while retaining enzymatic activity. Rosenblum et al. (1985) Cancer Res. 45, 2421 describes coupling human leukocyte interferon with an anti-interferon monoclonal antibody to increase the interferon's plasma half-life while maintaining its antiviral and antiproliferative properties.

Rijken et al. (1979) Biochim. Biophys. Acta. 580, 140 describes the partial purification, from human uterine tissue, of tissue plaminogen activator (t-PA), a single chain zymogenic enzyme activatable by plasmin in blood to a two-chain form which greatly accelerates the dissolving of fibrin clots. t-PA is thus useful as a therapeutic agent for dissolving clots in patients suffering from a variety of vascular diseases, particularly myocardial infarctions resulting in clots in and around the heart. Wei et al., U.S. Ser. No. 782,686, filed Oct. 1, 1985, assigned to the same assignee as this application and hereby incorporated by reference, describes the use of recombinant DNA techniques to produce human uterine t-PA.

A number of methods have been used to modify t-PA and other fibrinolytic enzymes (e.g., urokinase). Maksimenko et al. (1985) Thromb. Res. 38, 289 describes increasing the affinity of urokinase for fibrin clots by conjugating urokinase to fibrinogen; the resulting complex was subsequently incoporated into a fibrin clot during its natural formation. Maksimenko et al. (1985) Thromb. Res. 38, 277 describes a urokinase-sodium nitroprusside-heparin complex with simultaneous fibrinolytic, hypotensive, and anticoagulant effects. Sevilla et al. (1985) Biochim. Biophys. Res Commun. 130, 91 describes conjugating urokinase to polyclonal anti-human fibrinogen antibody through a bifunctional cross-linking reagent; the resulting conjugate had a strong binding affinity to human fibrinogen while retaining urokinase amidase activity. Ferres et al. E.P.A. 85100084.4 describes coupling t-PA and urokinase to human albumin, immunoglobin G, blocked plasmin, and fibrinogen through bifunctional cross-linking reagents; the resulting conjugates "retain fibrinolytic activity and have slow physiological clearance rates, and/or improved in vivo activity."

SUMMARY OF THE INVENTION

In general, the invention features a complex of a therapeutically effective enzyme and a monoclonal antibody specific for the enzyme, the antibody being bound to the enzyme at a site on the enzyme which does not substantially interfere with the activity of the enzyme (discussed below) and which increases the in vivo half-life of the enzyme.

The complex between the antibody and the enzyme must be tight enough so that the complex does not substantially dissociate in vivo. This tightness can be achieved in either of two ways: (1) the antibody and enzyme can be associated solely by immunoaffinity, provided that the $K_D$ (dissociation constant) of the antibody/enzyme complex is at least $10^{-11}M$, or (2) the antibody can be covalently bonded to the antigen by means of a cross-linking reagent. Covalent coupling can be used not only where the immunoaffinity of the antibody for the antigen is low, but also to reinforce a strong immune complex. Preferred enzymes are fibrinolytic enzymes, e.g., t-PA.

The therapeutic enzyme-monoclonal antibody complexes of the invention have an increased circulation half-life in vivo, compared to uncomplexed therapeutic enzymes, while maintaining therapeutic activity. Because of the increased half-life, a lower dosage of the therapeutic enzyme complex is required, thus reducing possible toxic effects associated with high dosages, and also lowering the cost of treatment.

Other features and advantages of the invention will be apparent from the following description of the preferred embodiment thereof and from the claims.

DESCRIPTION OF PREFERRED EMBODIMENTS

The drawing will first be described.

Drawing

The FIGURE is a graph representing the results of the analysis of two rabbits into which there was injected a monoclonal antibody-t-PA conjugate of the invention.

Structure

The general structure of the monoclonal antibody-therapeutic enzyme complexes of the invention will be described first, followed by a specific preperative example.

Enzyme Sites

According to the invention, monoclonal antibodies bind to enzymes in a way which takes into account two general types of sites found on enzymes: active sites, and sites involved in the in vivo half-life of enzymes.

All enzymes contain one or more active sites. Interference with these sites, e.g., by the covalent or non-covalent binding of an antibody at the sites, results in a decrease in the activity of the enzyme. Generally, physiologically acting enzymes have at least two different active sites: a site which is involved in the binding of the enzyme to its substrate, and a site involved in the actual enzymatic action of the enzyme. For example, t-PA has a fibrinogen binding site and a specific site responsible for clot-dissolving; interference with either site decreases t-PA's therapeutic clot-dissolving activity. Thus, to prevent enzyme inactivation, the monoclonal antibodies used in the invention should bind to the enzyme at a location on the enzyme which is not part of an active site.

Other important sites on an enzyme affect the enzyme's stability (i.e., half-life) in circulation. These sites can be of various types. Some such sites are associated with the clearance mechanism of the enzyme from circulation, generally acting as recognition sites for cells with a protein removing function, e.g., macrophages. Other such sites allow plasma enzymes to attach and degrade the enzyme. Thus, to enhance in vivo half-life, the monoclonal antibodies of the invention preferably interact with one or more of the stability-affecting sites so that the sites are masked, i.e., are not recognized by the entities normally responsible for promoting enzyme degradation or clearance from the circulation.

In order to test a monoclonal antibody to determine if it binds to the enzyme at a suitable site, the antibody is coupled to the enzyme and the resultant complex's half-life in plasma is measured, by standard techniques, and compared to the half-life of the uncoupled enzyme. If the half-life has increased by a desired amount, the activity of the complex is then measured, by standard tests, and compared to that of the uncoupled enzyme. If the activity of the enzyme has been substantially unaffected by the coupling process, the monoclonal antibody is suitable for use with the enzyme.

The coupling of the enzyme to the monoclonal antibody can be by any means which results in increased half-life in vivo. One class of reagents suitable for such coupling are bifunctional coupling reagents, which are described extensively in the patent and technical literature. Such reagents contain two reactive functionalities, one of which is capable of binding to the enzyme and one of which is capable of binding to the antibody. Homobifunctional cross-linking reagents are those in which the reactive functionalities are identical; heterobifunctional reagents are those in which the reactive functionalities are different. Examples of both types of bifunctional cross-linking reagents are given in Ferres et al., id and Maksimenko et al. (1985) Thromb. Res. 38, 289. The general coupling procedure involves first contacting the antibody with the enzyme so that the antibody is associated, by immunoaffinity, with an enzyme site, and then reacting the antibody-enzyme immune complex with the reagent to covalently bind the antibody to the enzyme at that site.

EXAMPLE

A t-PA-monoclonal antibody conjugate was prepared by the following method. Recombinant t-PA, prepared by the method of Wei et al., id, at $1.6 \times 10^{-6}$M in 0.5M $NH_4HCO_3$, was incubated with anti-t-PA monoclonal antibody, made according to standard techniques, present in a concentration of $1.6 \times 10^{-5}$M, at 37° for 1 hour. The solution was then extensively dialyzed into 0.1M $NaHCO_3$ (pH 8.5). Following dialysis, 0.01M disuccinimidyl suberate in dimethyl formamide was added to the mixture to a final concentration of $9 \times 10^{-5}$M. The resultant mixture was incubated at 37° for 30 minutes to yield the desired conjugate.

Use

EXAMPLE 1

The above-described conjugate was injected into rabbits via the marginal ear vein. At various times after injection, plasma samples were withdrawn through the carotid artery and analyzed for the presence of t-PA by the standard ELISA assay. The FIGURE shows the results from the analysis of a representative set of rabbits injected with different t-PA monoclonal antibody complexes (complex D and complex T). The percentage of t-PA remaining at time t was determined by dividing the amount of t-PA remaining at t by the amount of t-PA present at 30 seconds. As can be seen in the FIGURE, the amount of complexed t-PA remaining at 20 minutes ranged from 23-54%, while the amount of uncomplexed t-PA remaining at that time was only 1-2%.

EXAMPLE 2

The conjugate was also tested in the standard fibrin binding and amidolytic tests. The tests showed that the conjugate retained both fibrinolytic and amidolytic activity in plasma.

The monoclonal antibody-therapeutic enzyme complexes can be administered in the same manner as an uncomplexed enzyme. For example, t-PA-antibody will be admixed with a pharmaceutically acceptable carrier substance, e.g., saline, and administered orally, intravenously, or by injection into affected arteries or the heart. Administration will be generally as is carried out for t-PA alone and for two other blood clot lysing enzymes, streptokinase and urokinase. The following additional examples are illustrative.

EXAMPLE 3

For emergency treatment of thrombi by bolus injection, 5–10 mg of lyophilized t-PA antibody complex are mixed together with saline and placed in the chamber of a syringe, which is used to inject the t-PA/antibody complex bolus into the patient intravenously.

EXAMPLE 4

For infusion treatment for the rapid lysis of coronary thrombi, about 100 mg/hr of lyophilized t-PA/antibody complex are infused intravenously over a period of about 1 hour, followed by intravenous infusion of about 50 mg/hr over a period of about three more hours.

EXAMPLE 5

For infusion treatment for the rapid lysis of coronary thrombi, the protocol of Example 4 is followed, except that infusion is preceded by the intravenous injection of a bolus of about 10 mg t-PA/antibody complex in saline.

EXAMPLE 6

For infusion treatment for the slow lysis of deep vein thrombi about 15 mg/hr of lyophilized t-PA/antibody complex dissolved in saline are infused intravenously over a period of about 12–24 hours.

Other embodiments are within the following claims.

What is claimed is:

1. A pharmaceutical composition comprising a suitable carrier and a complex of the enzyme human tissue plasminogen activator and a monoclonal antibody specific for said enzyme, said antibody being bound to said enzyme by immunoaffinity, the $K_D$ of said antibody/enzyme complex being at least $10^{-11}$M, said antibody being bound to said enzyme at a site on said enzyme which does not substantially interfere with the activity of said enzyme and which increases the in vivo half-life of said enzyme.

2. A pharmaceutical composition comprising a suitable carrier and a complex of the enzyme human tissue plasminogen activator and a monoclonal antibody specific for said protein, said antibody being covalently bonded to said enzyme at a site on said enzyme which does not substantially interfere with the activity of said enzyme and which increases the in vivo half-life of said enzyme.

* * * * *